(12) United States Patent
Ryan

(10) Patent No.: US 10,918,377 B2
(45) Date of Patent: Feb. 16, 2021

(54) OPHTHALMIC WOUND CLOSURE DEVICES AND METHODS

(71) Applicant: Edwin Ryan, St. Paul, MN (US)

(72) Inventor: Edwin Ryan, St. Paul, MN (US)

(73) Assignee: Edwin Ryan, St. Paul, MN (US)

( * ) Notice: Subject to any disclaimer, the term of this patent is extended or adjusted under 35 U.S.C. 154(b) by 115 days.

(21) Appl. No.: 16/123,613

(22) Filed: Sep. 6, 2018

(65) Prior Publication Data

US 2019/0000442 A1    Jan. 3, 2019

Related U.S. Application Data

(60) Continuation of application No. 14/095,468, filed on Dec. 3, 2013, now abandoned, which is a division of application No. 12/895,058, filed on Sep. 30, 2010, now abandoned.

(60) Provisional application No. 61/247,818, filed on Oct. 1, 2009.

(51) Int. Cl.
| | |
|---|---|
| *A61B 17/04* | (2006.01) |
| *A61B 17/06* | (2006.01) |
| *A61F 9/007* | (2006.01) |
| *A61B 17/00* | (2006.01) |

(52) U.S. Cl.
CPC .......... *A61B 17/0482* (2013.01); *A61B 17/04* (2013.01); *A61B 17/06166* (2013.01); *A61F 9/007* (2013.01); *A61B 2017/00902* (2013.01); *A61B 2017/06176* (2013.01)

(58) Field of Classification Search
CPC ...... A61B 17/04; A61B 17/0482; A61F 9/007
See application file for complete search history.

(56) References Cited

U.S. PATENT DOCUMENTS

| | | |
|---|---|---|
| 2,818,866 A | 1/1958 | Thomas |
| 3,123,077 A | 3/1964 | Alcamo |
| 4,198,459 A | 4/1980 | Brumlik |
| 4,990,150 A | 2/1991 | Tsubota et al. |
| 5,021,057 A * | 6/1991 | Byrne, Jr. ............. A61B 17/04 606/107 |
| 5,718,708 A | 2/1998 | Webb |
| 5,951,565 A | 9/1999 | Freeman |
| 2003/0149447 A1 | 8/2003 | Morency et al. |
| 2004/0088003 A1 | 5/2004 | Leung et al. |
| 2004/0098122 A1 | 5/2004 | Lee et al. |
| 2005/0203554 A1 | 9/2005 | Dykes et al. |
| 2007/0038249 A1 | 2/2007 | Kolster |
| 2007/0257395 A1 | 11/2007 | Lindh et al. |
| 2008/0091224 A1 | 4/2008 | Griffis, III et al. |
| 2008/0221618 A1 | 9/2008 | Chen et al. |

(Continued)

OTHER PUBLICATIONS

"U.S. Appl. No. 12/895,058, Response filed Sep. 3, 2013 to Final Office Action dated Jul. 3, 2013", 11 pgs.

(Continued)

*Primary Examiner* — Alexander J Orkin

(74) *Attorney, Agent, or Firm* — Schwegman Lundberg & Woessner, PA.

(57) ABSTRACT

A method and device for wound closure is provided. One advantage of wound closure devices and methods shown includes a simple and inexpensive modified suture with increased pullout resistance to close wounds in eyes and prevent leakage. Another advantage includes a visualization tool to aid in locating the wound on the eye.

11 Claims, 5 Drawing Sheets

(56) References Cited

U.S. PATENT DOCUMENTS

2009/0105753 A1 4/2009 Greenhalgh et al.
2009/0281556 A1 11/2009 Newell et al.
2011/0213386 A1 9/2011 Ryan
2014/0094827 A1 4/2014 Ryan

OTHER PUBLICATIONS

"U.S. Appl. No. 12/895,058, Advisory Action dated Sep. 23, 2013", 3 pgs.
"U.S. Appl. No. 12/895,058, Final Office Action dated Jul. 3, 2013", 12 pgs.
"U.S. Appl. No. 12/895,058, Non Final Office Action dated Feb. 1, 2013", 9 pgs.
"U.S. Appl. No. 12/895,058, Non Final Office Action dated Jun. 20, 2012", 9 pgs.
"U.S. Appl. No. 12/895,058, Response filed May 1, 2013 to Non Final Office Action dated Feb. 1, 2013", 9 pgs.
"U.S. Appl. No. 12/895,058, Response filed Nov. 20, 2012 to Non Final Office Action dated Jun. 20, 2012", 5 pgs.
"U.S. Appl. No. 14/095,468, Advisory Action dated Nov. 15, 2016", 3 pgs.
"U.S. Appl. No. 14/095,468, Final Office Action dated Aug. 30, 2016", 7 pgs.
"U.S. Appl. No. 14/095,468, Final Office Action dated Dec. 6, 2017", 12 pgs.
"U.S. Appl. No. 14/095,468, Non Final Office Action dated Feb. 9, 2016", 7 pgs.
"U.S. Appl. No. 14/095,468, Non Final Office Action dated Jun. 20, 2017", 12 pgs.
"U.S. Appl. No. 14/095,468, Preliminary Amendment filed Dec. 4, 2013", 5 pgs.
"U.S. Appl. No. 14/095,468, Response filed Jan. 15, 2016 to Restriction Requirement dated Nov. 17, 2015", 6 pgs.
"U.S. Appl. No. 14/095,468, Response filed Jun. 9, 2016 to Non Final Office Action dated Feb. 9, 2016", 7 pgs.
"U.S. Appl. No. 14/095,468, Response filed Oct. 16, 2017 to Non Final Office Action dated Jun. 20, 2017", 10 pgs.
"U.S. Appl. No. 14/095,468, Response filed Oct. 31, 2016 to Final Office Action dated Aug. 30, 2015", 7 pgs.
"U.S. Appl. No. 14/095,468, Restriction Requirement dated Nov. 17, 2015", 5 pgs.

\* cited by examiner

OPHTHALMIC WOUND CLOSURE DEVICES AND METHODS

CLAIM OF PRIORITY

This application is a continuation of and claims the benefit of priority under 35 U.S.C. § 120 to U.S. patent application Ser. No. 14/095,468, filed Dec. 3, 2013, which is a division of and claims the benefit of priority under 35 U.S.C. § 120 to U.S. patent application Ser. No. 12/895,058, filed Sep. 30, 2010, which claims the benefit of priority under 35 U.S.C. Section 119(e) to Provisional Patent Application Ser. No. 61/247,818, filed Oct. 1, 2009 which are incorporated herein by reference in their entirety.

TECHNICAL FIELD

This invention relates to wound closure devices and methods to facilitate healing after an incision. Specifically, this invention relates to wound closure devices and methods for use in conjunction with ophthalmic surgery.

BACKGROUND

After some ophthalmic surgical procedures, the small incision, or wound, leaks after the surgical instrument is removed from the incision. One common procedure to reduce or stop leakage is to suture the incision. Knots tied in common suturing can be uncomfortable for the patient, and can be difficult and tedious for the surgeon. As with any difficult procedure there is some degree of risk to the patient. It can also be difficult to see where the wound is due to the small size of the wound.

What is needed is a device that aids in visualization of ophthalmic wounds. What is also needed is a device and method to reduce leakage through incisions following vitreous surgery that is easier, and more reliable. What is also needed is a device and method to reduce risk to the patient.

DETAILED DESCRIPTION

Figure 1A:
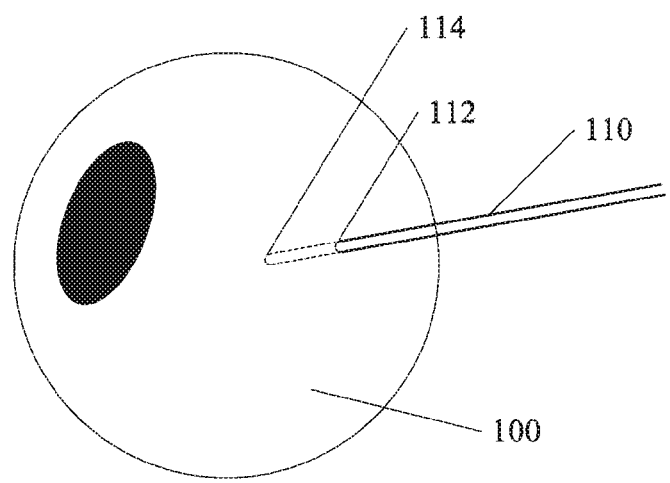
FIG. 1A shows a portion of an ophthalmic procedure according to an embodiment of the invention.

In the following detailed description, reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, mechanical, logical changes, etc. may be made without departing from the scope of the present invention.

FIG. 1A shows a portion of a procedure utilizing wound closure devices as described above. An eye 100 is shown. During a procedure, a cannula 110 is inserted into the eye through an incision 112 to reach a location 114 internal to the eye. Usually, an instrument is inserted through the cannula 110 to the location 114 in order to perform the desired procedure. Examples of instruments include, but are not limited to fiber optic probes, laser guides, suction/cutting tools, forceps, scissors, etc.

Figure 1B:
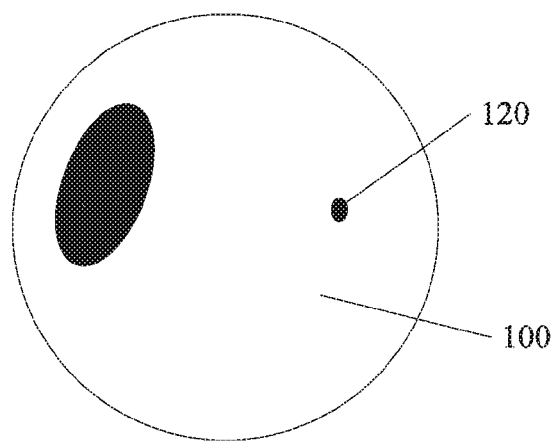
FIG. 1B shows another portion of an ophthalmic procedure according to an embodiment of the invention.

During a procedure, if the instrument (not shown) is removed from the cannula 110, a small plastic plug is inserted to control leakage from the cannula. However, at the end of the procedure, the cannula 110 is removed. FIG. 1B shows the eye 100 as shown in FIG. 1A after removal of the cannula 110. A wound 120 is shown where the cannula 110 passed through the sclera into the eye. In some procedures, the wound 120 leaks, and requires closure. Various configurations of devices are illustrated below to facilitate the closure.

Figure 2:
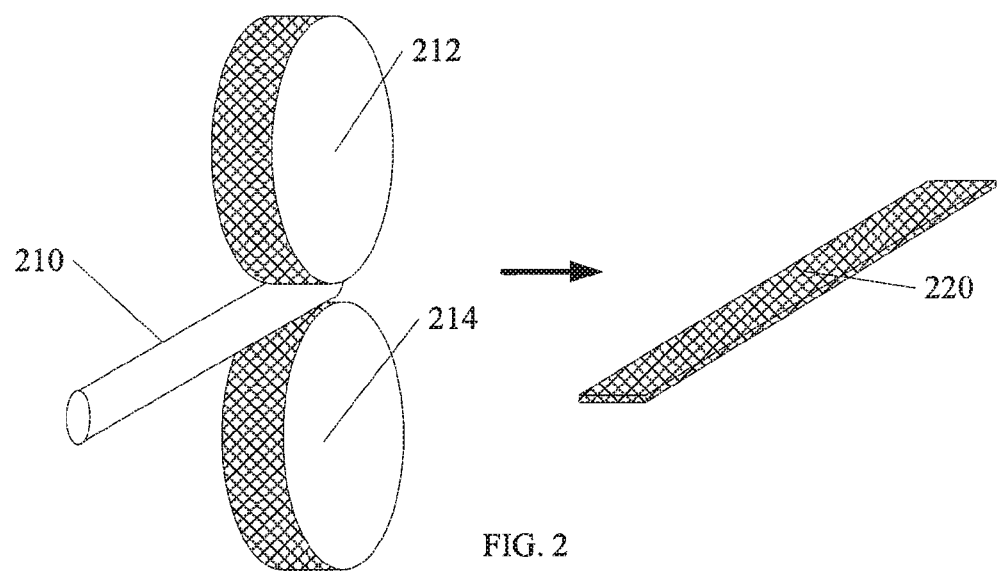
FIG. 2 shows forming a suture according to an embodiment of the invention.

FIG. 2 shows a standard round cross section suture 210. In the figure, one method of forming a modified suture is show. A wheel 212 or pair of wheels 212, 214 are used to flatten the suture 210 and form modified suture 220. In one example, a plain gut suture 210 is used. In one example, the flattening process provides a modified cross section that will crinkle or otherwise fold over on itself as it is drawn into tissue. The added friction of the modified suture provides a pullout resistance without the need for tying knots on the tissue. In one example, the rolling process further opens up a fiber structure within the suture and provides increased surface area to further increase friction and/or pullout resistance. In one example shown in FIG. 2, a pattern is pressed into the suture 210 to form modifies suture 220 with the pattern pressed into the suture 210 for added pullout resistance. An example of a procedure using a modified suture as shown in FIG. 2 or other figures is discussed in more detail below.

Figures 3A, 3B, 3C, 3D:
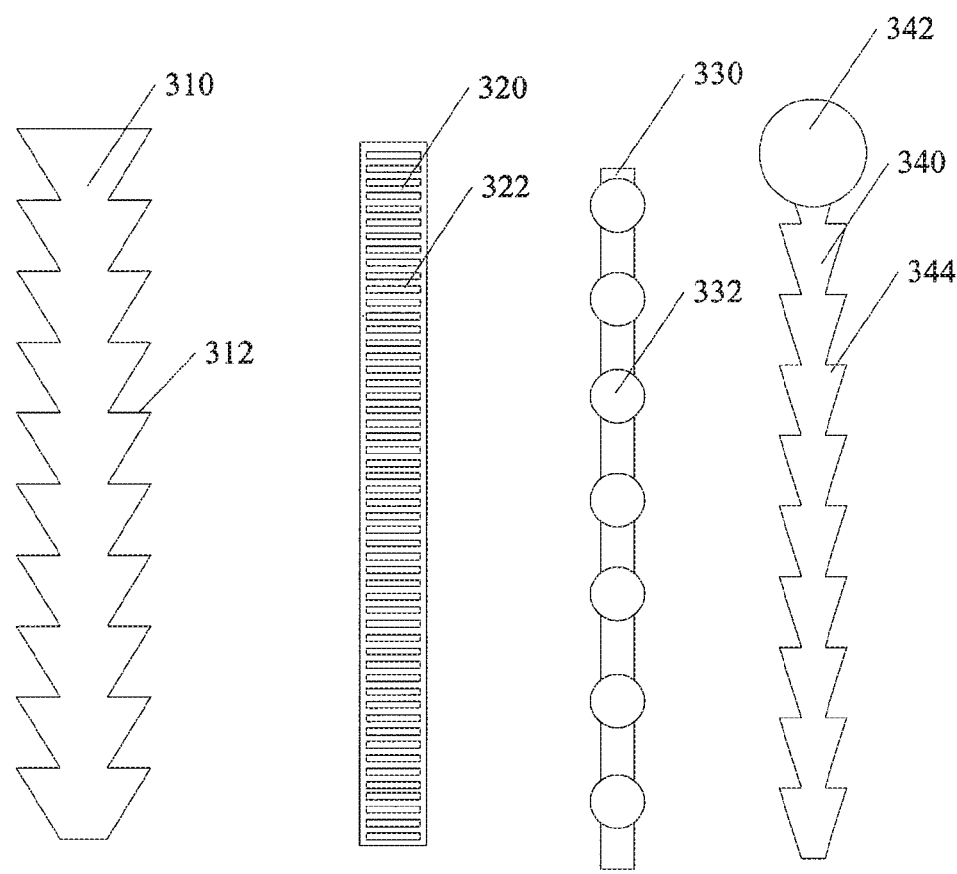
FIG. 3A-3D show example sutures according to embodiments of the invention.

FIG. 3A shows one example of a modified suture 310 according to an embodiment of the invention. A number of features such as one-way barbs 312 are shown on a side of the modified suture 310. FIG. 3B shows another example of a modified suture 320 according to an embodiment of the invention. A number of pressed features 322 such as knurls or other patterns are rolled into a surface of the suture to form a flattened, patterned modified suture 320. FIG. 3C shows another example of a modified suture 330 according to an embodiment of the invention. A number of knots 332 are pre-tied at various spacing along a length of the suture 330. The knots can be easily tied before a procedure, away from a patient, or they can be manufactured in place. Although knots 332 are described, other protrusions such as formed knobs, etc. may take the place of knots 332. FIG. 3C shows another example of a modified suture 340 according to an embodiment of the invention. A number of features such as one-way barbs 344 similar to those described in FIG. 3A are shown. A knot 342 or other protrusion is also shown at a distal end of the modified suture 340.

In selected examples such as modified sutures 320 and 330, an increased friction is provided in any direction to increase pullout resistance. In other selected examples such as modified sutures 310 and 340, the increased friction or pullout resistance is unidirectional. Barbs 312, 344 for example make the modified sutures 310, 340 easy to insert in one direction, and hard to pull back, once inserted.

In one example a biodegradable material is used for the modified suture, such as plain gut suture. Other materials such as PGA, etc. may also be used.

Figure 4:
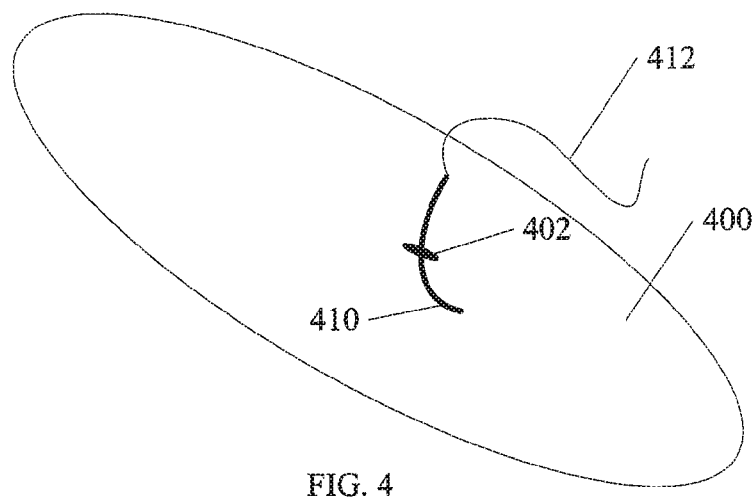
FIG. 4 shows use of a suture according to an embodiment of the invention.

FIG. 4 shows an example procedure using a modified suture according to an embodiment of the invention. A needle 410 is shown pulling a modified suture 412, through a location in the middle of a wound 402 in an eye 400. Although only one suture will be sufficient in many cases, the invention is not so limited.

Figure 5:
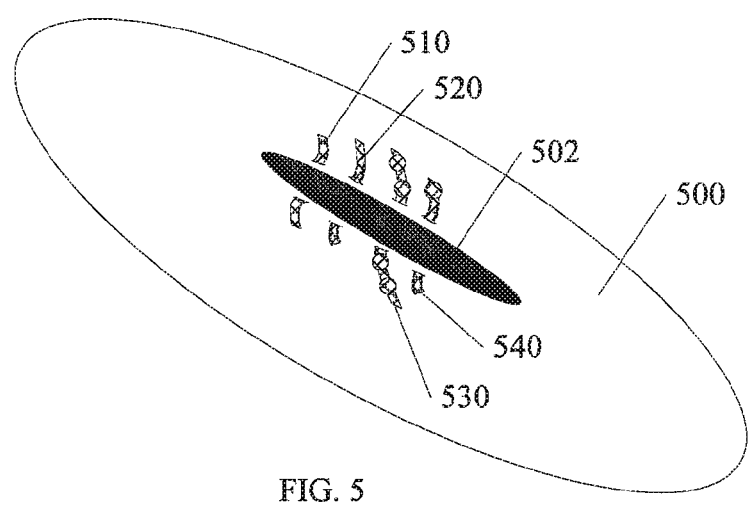
FIG. 5 shows example sutures in place on a wound according to embodiments of the invention.

FIG. 5 shows examples of modified sutures such as those shown in previous Figures. A first suture 510 is flattened to provide increased pullout resistance, and is pulled in from one side of a wound 502 in an eye 500 to the other side. No knot is tied. Only the increased pullout resistance holds the modified suture in place. Because ophthalmic wounds in such procedures do not require large forces to hold them closed, the addition of modified pullout resistance is enough to hold the modified sutures in place without a knot. In procedures where the modified suture is placed beneath the conjunctiva, the absence of a knot is more comfortable for the patient. Further, the absence of a knot makes the procedure much simpler for the surgeon to perform.

FIG. 5 also shows other examples of modified sutures in place. Modified suture 520 is shown with unidirectional barbs on side surfaces. Modified suture 530 shows a number of spaced knot to provide the increased pullout resistance. Modified suture 540 shows the unidirectional barbs in combination with a knot at a distal end. The modified suture 540 is therefore easy to install, and holds tight one in place due to the knot, and the barbs.

Figure 6:
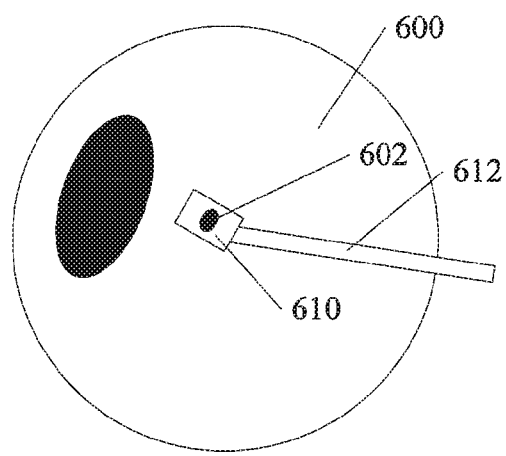
FIG. 6 shows a visualization device according to an embodiment of the invention.

FIG. 6 shows a visualization tool that is used to view a wound 602, and can be used by itself with standard suture practices, or can be used in conjunction with modified sutures as described above. The Figure illustrates a glass or plastic transparent portion 610 and a handle 612. It can often be difficult to visualize a small wound 602 due to fluids or blood present in the area, and the wound 602 itself being normally closed without any external pressure.

Using the visualization tool, pressure is put on the eye 600 in the general area of the wound 602. The pressure causes the fluids and/or blood to move away from the wound 602, and makes the wound 602 easier to visualize. Once the wound is located, the surgeon can proceed with suturing.

Figure 7:
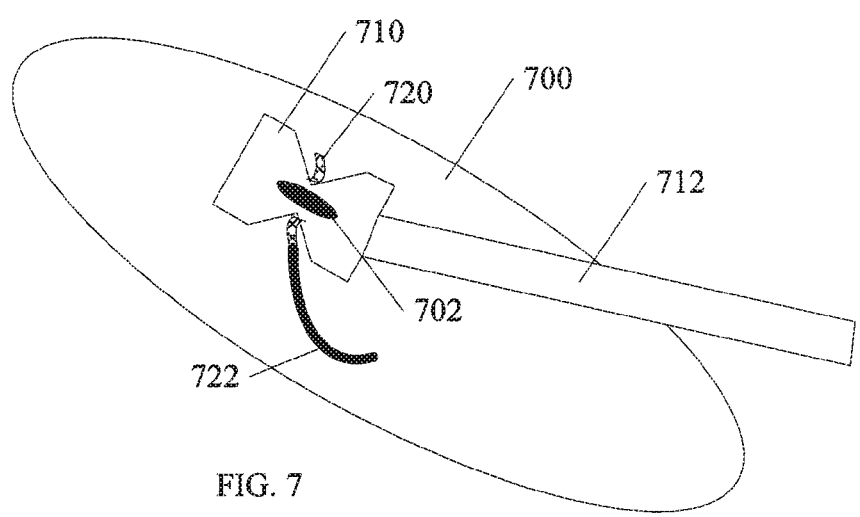
FIG. 7 shows another visualization device according to an embodiment of the invention.

FIG. 7 illustrates another example of a visualization tool that is particularly useful with the modified sutures described above. A transparent portion 710 is shaped thinner in the middle, for example as an hourglass shape. The wound 702 in the eye 700 is still visible as described in FIG. 6 above. However, due to the thinner middle of the transparent portion 710, a modified suture 720 can easily be inserted to close the wound 702 without having to remove the transparent portion 710. A needle 722 is shown pulling in the modified suture 720. An optional handle 712 is shown to better hold the transparent portion 710 and to put pressure on the eye 700.

Figure 8:
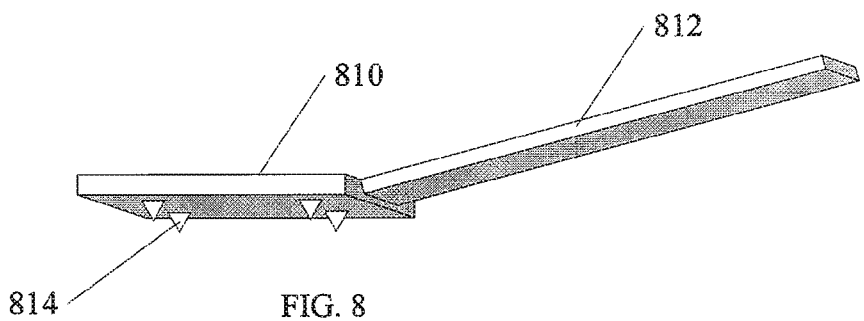
FIG. 8 shows another visualization device according to an embodiment of the invention.

FIG. 8 shows another example of a visualization tool that is particularly useful with the modified sutures described above. A transparent portion 810 is shown with an optional handle 812. Although an elongated handle 812 is illustrated, any number of handle configurations are within the scope of the invention. Likewise, a rectangular shape of the transparent portion 810 is shown, however shapes such as an hourglass shape described above, or other shapes are within the scope of the invention.

A number of teeth 814 or other frictional protrusions are shown on surface of the transparent portion 810 that is to be adjacent to the eye. By using teeth 814, a surgeon may grip the sclera of the eye with one hand to prevent rotation of the eye and aid in visualizing the wound simultaneously while the sutures are being placed with the other hand. The ability to grip the sclera is particularly useful in embodiments described above because of increased friction of the sutures in selected embodiments.

Figure 9:
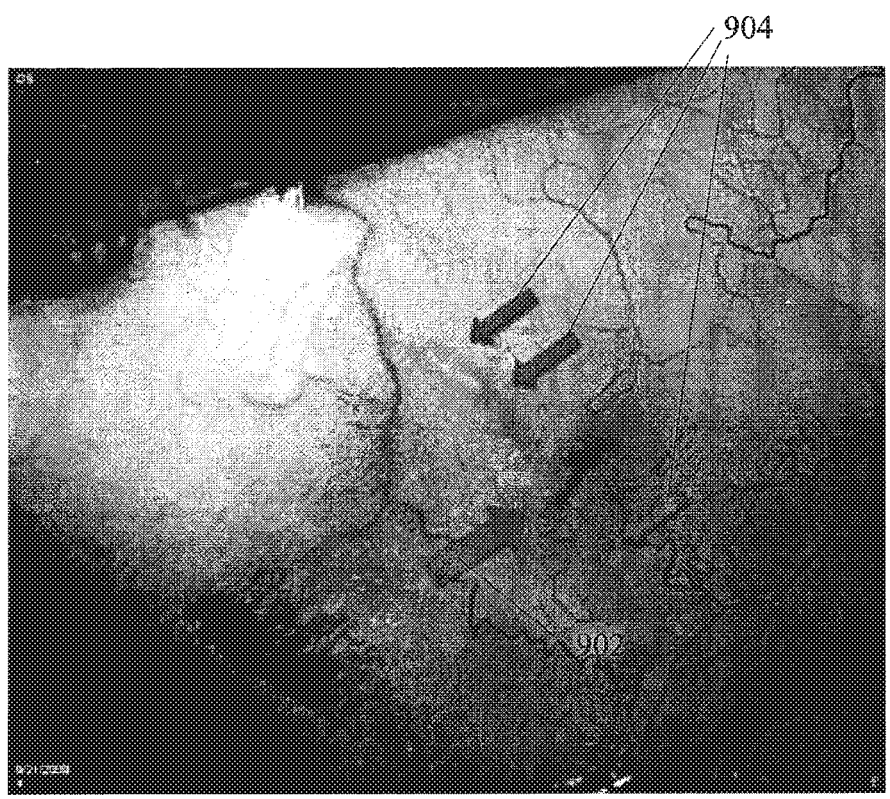
FIG. 9 shows an example of an eye after a procedure using devices and methods according to an embodiment of the invention.

FIG. 9 shows an example of an eye 10 days after a procedure as described above. Arrow 902 indicates the wound, while arrows 904 indicate sutures placed as described above.

Using embodiments described above, a number of advantages are realized. One advantage of wound closure devices and methods described above includes a simple and inexpensive alternative to knot tying after suturing to prevent leakage. Another advantage includes a biocompatible material that degrades over time to allow healing of the incision. Although suture procedures involving the eye are disclosed, any other suture location would benefit from the devices and methods disclosed.

Although selected advantages are detailed above, the list is not intended to be exhaustive. Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. It is to be understood that the above description is intended to be illustrative, and not restrictive. Combinations of the above embodiments, and other embodiments will be apparent to those of skill in the art upon reviewing the above description. The scope of the invention includes any other applications in which the above structures and fabrication methods are used. The scope of the invention should be determined with reference to the appended claims, along with the full scope of equivalents to which such claims are entitled.

What is claimed is:

1. A method, comprising:
   pressing a transparent portion of a visualization device in direct contact with an ophthalmic wound;
   moving fluids away from the ophthalmic wound as a result of pressure from the transparent portion to enhance visualization of the ophthalmic wound; and
   suturing the ophthalmic wound while maintaining pressure of the transparent portion against the ophthalmic wound, wherein the transparent portion of the visualization device is thinner in a middle suture clearance cutaway region that facilitates insertion of a suture through the suture clearance cutaway region while the substantially transparent portion is in contact with the eye.

2. The method of claim 1, wherein the transparent portion of the visualization device includes a pair of adjacent suture clearance cutaways that facilitates insertion of a suture while the substantially transparent portion is in contact with the eye; and suturing through the suture clearance cutaway.

3. The method of claim 1, further including engaging one or more frictional protrusions located on one side of the transparent portion with an eye to hold the transparent portion in place while suturing.

4. The method of claim 3, wherein engaging one or more frictional protrusions includes engaging one or more teeth.

5. The method of claim 1, wherein the transparent portion of the visualization device includes holding a handle attached to the transparent portion and applying pressure with the handle.

6. The method of claim 1, wherein suturing the ophthalmic wound includes suturing with a portion of suture having a flattened cross section to enhance a suture pullout resistance.

7. The method of claim 6, wherein suturing the ophthalmic wound includes suturing with a portion of suture having one or more textured side features.

8. The method of claim 1, wherein suturing the ophthalmic wound includes suturing with a portion of suture having a number of unidirectional, pressed in, side features to increase a pullout resistance of the suture along a first direction.

9. The method of claim 8, wherein suturing the ophthalmic wound includes suturing with a portion of suture having a distal end protrusion to resist suture pullout from a second direction opposite the first direction.

10. A method, comprising:
pressing a transparent portion of a visualization device in direct contact with an ophthalmic wound that is normally closed without any external pressure;
moving fluids away from the ophthalmic wound as a result of pressure from the transparent portion to enhance visualization of the ophthalmic wound; and
suturing the ophthalmic wound while maintaining pressure of the transparent portion against the ophthalmic wound, wherein the transparent portion of the visualization device is thinner in a middle suture clearance cutaway region that facilitates insertion of a suture through the suture clearance cutaway region while the substantially transparent portion is in contact with the eye.

11. The method of claim 10, wherein the transparent portion of the visualization device includes a pair of adjacent suture clearance cutaways to facilitate insertion of a suture while the substantially transparent portion is in contact with the eye; and suturing through the suture clearance cutaway.

* * * * *